United States Patent [19]  [11] 4,333,941
Baratz et al.  [45] Jun. 8, 1982

[54] INHIBITION OF ENVELOPED VIRUSES WITH PHENYL KETONES

[75] Inventors: Brenda S. Baratz; Robert A. Phillips, both of Indianapolis; David L. Steward, Carmel, all of Ind.

[73] Assignee: The Dow Chemical Company, Midland, Mich.

[21] Appl. No.: 839,056

[22] Filed: Oct. 3, 1977

Related U.S. Application Data

[63] Continuation of Ser. No. 643,585, Dec. 22, 1975, abandoned.

[51] Int. Cl.³ .................. H61K 27/00; A61K 31/445; A61K 31/135
[52] U.S. Cl. .............................. 424/267; 424/248.57; 424/248.58; 424/330
[58] Field of Search ........................................ 424/267

[56] References Cited

PUBLICATIONS

Ship et al., Oral Surgery, Oral Medicine and Oral Pathology, vol. 13, No. 5, 1960, pp. 630–631.
Catalog, Dow Pharmaceuticals, The Dow Chemical Co., Aug. 1972.

Primary Examiner—Jerome D. Goldberg

[57] ABSTRACT

Enveloped viruses such as rhabdoviruses, herpes viruses, influenza viruses, α viruses and paramyxo viruses are inactivated by contacting the viruses or virus infected cells with a β-aminophenylketone compound such as 4-n-butoxy-β-(1-piperidyl)propiophenone hydrochloride; 3,4-dichloro-β-(1-piperidyl)propiophenone; 4-n-decyloxy-β-(1-piperidyl)propiophenone; or 4-n-butoxy-β-(N,N-diethylamino)propiophenone.

26 Claims, No Drawings

INHIBITION OF ENVELOPED VIRUSES WITH PHENYL KETONES

CROSS-REFERENCE TO RELATED APPLICATION

This is a continuation of application Ser. No. 643,585 filed Dec. 22, 1975 and now abandoned.

BACKGROUND OF THE INVENTION

The compounds used in the present invention be prepared by the known methods such as those described in Profft, *Chem. Tech.* (*Berlin*) 4, 241 (1952); and Bockstahler, U.S. Pat. No. 2,771,391, or by procedures analogous thereto. One of the β-aminopropiophenones, 4-n-butoxy-β-(1-piperidyl)-propiophenone hydrochloride is also known by the generic name dyclonine hydrochloride. Dyclonine hydrochloride is used as a topical anesthetic with antibacterial and antifungal properties. See, Florestano, U.S. Pat. No. 2,868,689, and Remington's *Pharmaceutical Sciences,* Thirteenth Ed., Mack Publishing Co. Easton, Pa. (1965) page 1142. Many of the other β-aminopropiophenones also are known to have topical anesthetic activity, U.S. Pat. No. 2,771,391.

Dyclonine hydrochloride has been used as a topical anesthetic in oral conditions involving herpes simplex virus type I (HSV-I) infections. Ship et al., *Oral Surgery, Oral Medicine and Oral Pathology,* Vol. 13, No. 5, pages 630-636, (May 1960). Ship et al. describe adequate anesthesia of acute herpetic gingivostomatitis lesions using solutions containing 0.5 percent dyclonine hydrochloride, an amount sufficient for oral anesthesia. It has also been used as an anesthetic for application to a variety of lesions, and as an anesthetic in proctology and in gynecology for relief of pain of episiotomy or perineorrhaphy.

BRIEF SUMMARY OF THE INVENTION

The present invention concerns a method useful for inactivating viruses, and is more particularly concerned with inactivating viruses by contacting enveloped viruses with an effective amount of a β-aminophenylketone compound corresponding to one of the formulae

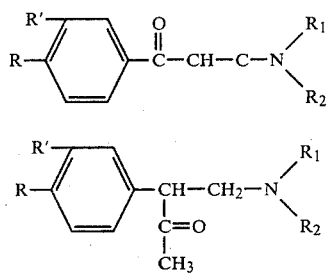

wherein R represents hydrogen, halo, or alkoxy of from one to twelve carbon atoms, R' represents hydrogen or halo; $R_1$ and $R_2$ represent loweralkyl, or $R_1$ and $R_2$ taken together with the nitrogen atom represent a heterocyclic amino group or an N-loweralkyl quaternary heterocyclic ammonium group wherein the heterocyclic amino or ammonium group has four, five or six carbon atoms and zero or one ring hetero-atom in addition to said nitrogen selected from oxygen, sulfur and nitrogen; or $R_1$ and $R_2$ taken together with the nitrogen atom represent tri-loweralkyl-ammonium and the pharmaceutically-acceptable salts thereof. As employed herein, "halo" refers to fluoro, chloro, bromo and iodo, chloro being preferred, and "loweralkyl" refers to loweralkyl of one to six carbon atoms.

The $-NR_1R_2$ moiety of formulae I and II can thus be represented by the following partial formulae:

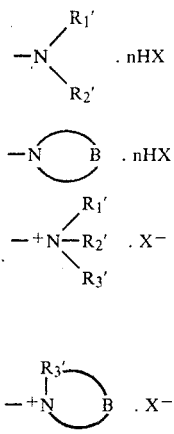

and

wherein $R_1'$, $R_2'$ and $R_3'$ are each loweralkyl, X (in HX and $X^-$) represents a pharmaceutically acceptable anion, and represents a heterocyclic amino group of four to six carbon atoms and zero or one additional hetero atom selected from sulfur, oxygen and nitrogen.

Preferred groups include: for R, alkoxy; for R', hydrogen or halo, for $-NR_1R_2$, diloweralkyl amino, piperidino, morpholino and —N-loweralkyl piperidinium. Compounds of Formula I are preferred over those of Formula II, both broadly and with one or more of the above preferred substituents. Hydrohalide acid addition salts, particularly the hydrochlorides, are preferred.

For convenience, such compounds will be hereinafter referred to as "phenylketones".

The phenylketone compounds are crystalline solids which are soluble in a variety of conventional liquids, including alcohols, chlorinated hydrocarbons, etc. In general the pharmaceutically-acceptable salts are more soluble in aqueous liquids than are the free base compounds, and the compounds are preferably employed in the form of such salts.

As employed herein, the phrase "pharmaceutically-acceptable salt" refers to salts of the phenylketones the anions of which are relatively non-toxic and innocuous to mammals at dosages or concentrations consistent with good antiviral activity so that side effects ascribable to the anions do not vitiate the beneficial effects of the phenylketones. Suitable pharmaceutically-acceptable salts which can be employed in the method and composition of the invention include those derived from mineral acids such as the hydrochloride, hydrobromide, phosphate, nitrate and sulfate salts, those derived from organic carboxylic acids such as the succinate, tartrate, citrate, malate, maleate, and acetate salts and those derived from organic sulfonic acids such as the methanesulfonate and toluenesulfonate salts.

In practicing the method, an enveloped virus is contacted with one or more of the phenylketones in an amount sufficient to inactivate the virus. Contacting can be carried out in vitro, in the absence of living tissue, for example, by contacting non-living substrates contaminated with virus. In vitro operations can be useful to inactivate viruses in contaminated liquids such as solutions or suspensions, for example, in saliva, urine or in virus culture media for protein coated viruses such as picorna viruses, to inhibit contaminating enveloped viruses. In vitro operations can also be used for solid substrates and surfaces such as bedding, garments; dental equipment, vaginal speculae, forceps, examination tables, gloves, milking machines, poultry cages and the like which may become contaminated with infective enveloped viruses, such as herpes simplex, influenza, infectious bovine rhinotracheitis, Newcastle's disease virus. Also the active compounds can be incorporated in air filters, screens or the like to inactivate air borne viruses passed therethrough.

The contacting of enveloped virus and phenylketone compound can also be carried out in vivo, by administering an effective amount of the phenylketone compound to a mammal infected with enveloped virus, in a manner effective to result in contact and exposure of the virus to a virus inhibiting amount of the compound. The compounds can be administered orally, parenterally (usually by injection) or topically. Dyclonine hydrochloride, for example, has been administered in anesthetic studies, intravenously at dosages of up to 7 milligrams compound per kilogram of body weight ("mg/kg") with no notable anesthetic effects, and orally at doses up to about 17 mg/kg also with no notable anesthetic effect. It has an acute $LD_{50}$ in mice of 19.5 mg/kg intravenous and 52.8 mg/kg by intraperitoneal injection. Topical application permits use of higher phenylketone concentrations directly at infected sites, such as genital herpes virus type 2 ("HSV-2") lesions, or intact genital mucosa infected or contaminated with HSV-2, without prior distribution of compound through uninfected parts of the mammalian system. Topical application of the phenylketones is preferred.

The amount of the phenylketone compound to be employed can be referred to as an "antiviral amount", "viral inhibiting amount", or "effective amount to inhibit viruses", etc., it being understood that sufficient compound is employed to achieve significant viral inhibition. The antiviral amount of compound, that is, the amount of the phenylketone compound sufficient to provide the desired effect depends on various known factors such as type of contacting, in vitro or in vivo operations, concentration of phenylketone, exposure time (contact time), type of virus involved, degree of viral contamination or infection, the size, type, age and condition of the animal to be treated, locus of infection in the animal, the particular compound of pharmacologically-acceptable salt employed, the route and frequency of administration, the degree of inhibition desired, and whether or not topical anesthetic action is also desirable. In particular cases, the amount to be administered can be ascertained by conventional range finding techniques, for example, by observing the effect produced at different treatment rates using conventional virus assay procedures.

In practicing the method of the invention, the active ingredient is preferably incorporated in a composition comprising a suitable carrier and from about 0.0001 molar to about 95 percent by weight of the phenylketone compound or a pharmacologically-acceptable salt thereof. Suitable carriers include pharmaceutical carriers, that is, known solid or liquid pharmaceutical excipients useful in formulating pharmacologically-active compounds for internal or external administration to animals, and which are substantially non-toxic and non-sensitizing under conditions of use. Suitable carriers for in vitro use can also include conventional disinfectant formulations, detergents, etc. which are chemically compatible with the phenylketones but which need not be suitable for in vivo use.

Suitable pharmaceutical carriers are known and disclosed in texts such as Remington's Pharmaceutical Sciences, Thirteenth Ed., Martin (Ed.) Mack Publishing Co., Easton, Pa. (1965). The compositions can be prepared by known techniques for the preparation of tablets, capsules, lozenges, troches, creams, ointments, emulsions, suppositories dispersions, topical foams, wettable and effervescent powders, sterile injectable compositions, and can contain suitable excipients known to be useful in the preparation of the particular type of composition desired.

Preferred compositions include compositions containing from about 0.0025 to about 0.05 to about 0.25, to about 0.5 to about one to about 10 percent to about 25 percent by weight of phenylketone in a carrier. Generally, topical compositions containing from about 0.0025 to about 0.25 percent phenylketone in a topically acceptable pharmaceutical carrier have low anesthetic effect, and are preferred when topical anesthesia is to be avoided, and higher concentrations (0.5 to 5 percent) are used when concurrent anesthesia and antiviral action are desired. Concentrations of one to 25 to 95 percent are useful in concentrates to be diluted before use and in in vitro applications.

The method of the invention is useful in inhibiting or inactivating enveloped viruses, (also classifiable as ether sensitive virus or lipid containing viruses) such as rhabdo, herpes, influenza, α and paramyxo viruses. Picorna viruses with protein coats, (ether resistant viruses) such as rhino virus and polio virus appear to be relatively insensitive to contact with the phenylketones. Vaccinia virus is affected, but is much more resistant than enveloped viruses. Electron microscopy indicates that contact of enveloped virus with the phenylketones results in substantially complete rupture of the viral envelope and release of viral nucleoproteins. However, it is understood that the invention is not limited to a particular mechanism or theory of viral inactivation.

A particularly advantageous feature of the invention is the discovery that the phenylketones are effective against herpes simplex virus type 2 ("HSV-2"). HSV-2 is frequently involved in urogenital infections, the affected organs being the cervix, vulva, vagina, urethra in females and penis and urethra in males. It has also been involved in localized and generalized infections of newborns, the infection usually being transmitted during delivery on passage through the infected birth canal. HSV-2 infections have been recently recognized as a common venereal disease. See, Nahmias and Roizman, New England Journal of Medicine, 289(15): 781 (1973). HSV-1 is more commonly involved in oral, labial and ocular infections and is immunologically different from HSV-2. See, Nahmias and Roizman, supra, and Stalder et al., Journal of Infectious Diseases, 131(4): 423 (1975). Infectious virus can be transmitted by contact, through contaminated body fluids, air droplets or through medical or dental implements which have contacted the infected sites.

Inactivation of herpes viruses in vitro by means of the invention can be useful in controlling transmission of the virus. Inactivation of genital herpes virus, particularly HSV-2, by contacting genital herpes lesions or preferably by contacting intact but infected (or contaminated but uninfected) genital cutaneous mucosa with one or more of the phenylketones, can also be useful in controlling or inhibiting transmission of virus both between hosts and between different sites in the same host, or between mother and newborn and can also be useful in alleviating the infection. The local anesthetic effect of the phenylketones, particularly dyclonine hydrochloride can provide symptomatic relief from local irritation at the infected lesions. In some situations, the invention is advantageously employed by contacting infected skin or mucous membrane or contaminating viruses on uninfected skin or mucous membrane, with an antiviral amount less than an anesthetic amount of the phenylketone, to bring about viral inhibition without anesthesia. In the latter situations the compounds are preferably employed in solutions, or suspensions or lotions such as soap or detergent cleansers, rinses, lotions, douches, skin creams, alcoholic solutions, aqueous solutions, etc. at concentrations from about 0.001 percent by weight to about 0.1 to 0.3 percent by weight.

The following Examples illustrate the invention.

EXAMPLE 1—Inactivation of HSV-I

Solutions containing 20,000, 10,000, 5,000, or 1,250 micromolar concentrations ($10^{-6}$ mole per liter, "$\mu M$") of various test compounds were prepared using triple distilled water. One tenth milliliter (0.1 ml) of each test solution was mixed with nine-tenths milliliter (0.9 ml) of tissue culture medium containing infective virus in concentrations of $10^4$ to $4\times10^7$ plaque forming units per milliliter. (The resulting test compound concentrations were thus 2000, 1000, 500 and 125 $\mu M$.) The mixtures were incubated for one hour at 37° C., after which the amount of infective virus remaining was determined by plaque assay on Vero or HeLa cells. Triple distilled water with no test compound was used as a control for comparison, and results were calculated as percent of virus surviving the test compound with 100 percent representing the results obtained with the triple distilled water control. Using HSV-1 virus, the results were obtained, plotted graphically against concentration, and the concentration of various test compounds required to give 50 percent virus inhibition (less than 50% survival) were determined. These results are set out below:

| Compound | Concentration Producing 50% Virus Inhibition (micromolar) |
| --- | --- |
| Dyclonine . HCl | 125 |
| 4-Methoxy-3-piperidino propiophenone . HCl | 125 |
| 3-Phenyl-4-piperidino-2-butanone . HCl | 550 |
| 3',4'-Dichloro-3-piperidino-propiophenone . HCl | <125* |
| 3'-Chloro-3-piperidino-propiophenone . HCl | 125 |
| 4'-Ethoxy-3-piperidino-propiophenone . HCl | 1500 |
| 4'-Propoxy-3-piperidino-propiophenone . HCl | 400 |
| 4'-Isobutoxy-3-piperidino-propiophenone . HCl | 200 |
| 4'-Hexyloxy-3-piperidino-propiophenone . HCl | <125 |
| 4'-n-Octyloxy-3-piperidino-propiophenone . HCl | <125 |
| 4'-n-Decyloxy-3-piperidino-propiophenone . HCl | <125 |
| 4'-Butoxy-3-diethylamino-propiophenone . HCl | <125 |
| 4-Butoxy-3-morpholino-propiophenone . HCl | 125 |
| 1-[2-(4-butoxybenzoyl)-2-methylethyl]-1-methyl-piperidinium iodide | >750** |
| 1-[2-(4-butoxybenzoyl)-ethyl]-1-methyl piperidinium iodide | <125 |
| benzocaine*** | >2000** |
| procaine . HCl | >2000 |
| lidocaine . HCl | >2000 |
| dibucaine . HCl | 800 |
| phenacaine . HCl | >2000 |
| tetracaine . HCl | >2000 |
| proparacaine . HCl | >2000 |
| benoxinate . HCl | >2000 |
| pramoxine . HCl | 675 |

<indicates "less than", 50% inhibiting concentration below stated concentration
**>indicates "greater than"; 50% inhibiting concentration above stated figure.
***known local anesthetics included for comparison

EXAMPLE 2

In a procedure similar to that of Example I, dyclonine hydrochloride was employed as a test compound against the enveloped viruses-VSV (vesicular stomatitis virus), HSV-1, SFV (semliki forest virus), influenza, and NDV (Newcastle's disease virus) the picorna viruses rhinovirus and poliovirus (viruses with a protein coat, rather than an envelope) and vaccinia virus. Fifty percent inactivation of the enveloped viruses was obtained at concentrations of 1000 $\mu M$ or below. Vaccinia virus was 50 percent inactivated at 2000 $\mu M$ or less, and the picorna viruses were less than 50 percent inactivated. 500 $\mu M$ of dyclonine hydrochloride gave greater than 99 percent inactivation of VSV, greater than 90 percent inactivation of HSV, and about 80 percent inactivation of influenza virus in the one hour exposure period.

EXAMPLE 3

Using dyclonine hydrochloride as a test compound in the procedure of Example I, two strains of HSV-1 and one strain of HSV-2 were studied. Ninety nine percent inactivation was evident with all viruses at concentrations below 1000 $\mu M$. Greater than fifty percent inactivation of HSV-2 was obtained with a concentration of 250 $\mu M$ dyclonine hydrochloride.

EXAMPLE 4

Purified concentrated PR8 strain influenza virus (about $10^{11}$ PFU/ml) was prepared according to Chow and Simpson, Pro. Nat'l. Acad, Sci. 68, 752–756 (1961) with the variation that in the final step virus was banded in a 15–45% sodium-potassium tartrate gradient instead of a sucrose gradient. The purified virus in tris.HCl pH 7.4 buffer was mixed with an equal volume of aqueous dyclonine hydrochloride to provide ultimate concentrations of 7500 and 1000 $\mu M$. Water was used as a control. After one hour incubation at 37° C. samples were prepared for electron microscopy by uranyl acetate negative staining. Changes in the viral envelope in the 1000 $\mu M$ exposure specimen were noted, as compared to the control. The samples from virus exposed to 7500 $\mu M$ dyclonine hydrochloride showed almost complete rupturing of the viral envelope and release of viral nucleoprotein strands.

EXAMPLE 5—In Vivo Treatment of HSV-1

Guinea pigs were prepared by removal of dorsal hair and infection of the shaved area by vaccination with HSV-1, Stohr strain in twelve inoculation sites. The procedure used was similar to the procedure of Hubler et al. J. Invest. Dermatol., 62: 92–95 (1974). Ten guinea pigs were inoculated. One hour after inoculation the animals were treated by topical application to the infected shaved area of either (a) 2 percent dyclonine hydrochloride in 5 percent ethanol in water or (b) a placebo consisting of 5 percent ethanol in water. Application was repeated hourly for four days, and the inoculation sites were observed daily for herpes lesions by five independent observers. Where lesions appeared in the shaved area, treatment included application to the lesions as well as the surrounding skin. The treatment solutions were coded to provide a double blind experiment with five animals receiving dyclonine hydrochloride and five receiving placebo.

In placebo treated animals, herpes lesions were first observed 48 hours after inoculation and by the sixth day after inoculation lesions were observed at virtually all of the inoculation sites (60 sites in 5 animals) in all placebo treated animals. In the dyclonine hydrochloride treated guinea pigs, significantly fewer lesions were observed at 48 hours after inoculation (31 percent of the sites, versus 88 percent of the sites in the placebo group). The lesions noted at 48 hours disappeared rapidly, to 7 percent of the sites by 72 hours, and no lesions were noted in the dyclonine-treated animals on days 5 to 6.

EXAMPLE 6

A. One percent dyclonine hydrochloride is mixed with a blend of 60 percent polyethylene glycol 200 dilurate and 10 percent polyethylene glycol 200 distearate and 30 percent mineral oil to make a water dispersible ointment.

B. 0.5 Percent dyclonine hydrochloride is dissolved in aqueous 0.3 percent chlorobutanol and the solution is adjusted to pH 4.0 with hydrochloric acid to make an aqueous preparation suitable for topical use in vivo or for in vitro use on non-living surfaces.

C. 5 Percent by weight dyclonine hydrochloride is dissolved in rubbing alcohol NF with about 0.5 percent thymol for use as a disinfectant and inactivator of enveloped viruses on non-living substrates.

D. An ointment base is prepared by blending equal parts of polyethylene glycols 4000 and 400 at 70° C., then cooling to room temperature. The base is blended with dyclonine hydrochloride to provide ointments containing 0.5, 2 and 5 percent of the active ingredient.

EXAMPLE 7

In a procedure similar to that of Example 5, dyclonine hydrochloride was employed as a 15 percent solution in a glycol salicylate carrier. Good control of the HSV-1 virus infection was obtained, however, skin irritation attributed to the vehicle was observed in both placebo and dyclonine treated animals.

In another operation similar to that of Example 5, dyclonine hydrochloride was employed under an occlusive bandage in a regimen involving change of bandage and repeated treatment every 6 hours. Antiviral effects were observed, however, a Candida (yeast) infection developed. The yeast infection was attributed to presence of C. albicans as normal dermal flora in guinea pigs and inhibition of competing skin bacteria by the experimental treatment. The results indicate the desirability of using an antimycotic agent in combination with dyclonine when fungi, as well as viruses, may be present.

EXAMPLE 8—In vivo Treatment of Genital Cutaneous Mucosa-HSV-2

The general inoculation procedure of Example 5 was used to inoculate the mucoid cutaneous genital area of both male and female mature guinea pigs with a suspension of HSV-2 virus. This procedure produces a genital herpes infection with genital lesions appearing in 48–72 hours. In untreated animals the HSV-2 infection progresses to involve hind limb paralysis and death.

Three groups of guinea pigs were thus inoculated with HSV-2. Treatment was begun one hour after inoculation, and was repeated on the first day hourly from 11:00 a.m. to 7 p.m., followed by three treatments at hourly intervals beginning at about 9:30 p.m. Treatment on the second day consisted of ten treatments at one to two hour intervals over the period 7:00 a.m. to 9:00 p.m. On the third day, seven treatments at one to two hour intervals, from 7:00 a.m. to 9:00 a.m. were employed. On the fourth and fifth days, there were five treatments per day at one to two hour intervals between 7:00 a.m. and 3:00 p.m. Treatments were then discontinued, although the animals were observed daily from the first through the eighth day. Treatment was topical application to the infected genital dermal mucosa of (a) 2 percent dyclonine hydrochloride in 5 percent aqueous ethanol (test group-four male and four female); or (b) 5 percent aqueous ethanol (placebo group-four male and three female). The third group of animals (four male and three female) were left untreated to serve as a control group. By 72 hours after inoculation genital herpes lesions were evident in all the placebo and control animals, and no lesions were present in the test group. On the eighth day, the same pattern had continued, with seven to twenty lesions on each of the surviving control and placebo animals, and no lesions or symptoms of herpes infection being observed in the dyclonine hydrochloride treated animals. No irritation or other adverse effects attributable to the dyclonine treatment were noted, although hyperkeratosis was noted in all the animals. (Animals in the placebo and control group which developed hind limb paralysis and severe infection were euthanized when obviously moribund.)

EXAMPLE 9

In a procedure similar to that of Example 8, dyclonine hydrochloride was applied topically to HSV-2 infected genital mucoid cutaneous tissue, (including vulvular mucosa) in female guinea pigs. In this operation, three groups (A, B, and C) of five animals each were treated by topical application to the infected tissue of two percent dyclonine hydrochloride in aqueous 5 percent ethanol. A fourth group was left untreated as a control.

In group A, treatment was begun one hour after inoculation and repeated at two hour intervals for a total of six applications on the first day. On the second and third days topical application was carried out seven times daily at two hour intervals from 8:00 a.m. to 8:00 p.m. No treatment was administered thereafter.

In group B, treatment was begun one hour after inoculation, repeated two hours later, followed by two more treatments at four hour intervals on the first day. On the second, third and fourth days, dyclonine treatment was carried out four times daily at four hour intervals beginning at 8:00 a.m. Three treatments at four hour intervals were made on the fifth day, then dyclonine administration was terminated.

In group C, the first topical application of dyclonine hydrochloride was made about 24 hours after inoculation (on the second day). Seven applications daily at two-hour intervals were made on the second through the fourth day, and five applications at two hour intervals were made on the fifth day, after which treatment was terminated.

In the control group, four guinea pigs developed HSV-2 genital lesions by the third day after inoculation. The infection progressed through the seventh day with spreading lesions, swelling, exudation and eventually hind limb paralysis.

In a group A, no lesions were observed in any of the animals until the fifth day, two days after cessation of treatment. At this time a single lesion was noted in a single animal. On days 6 and 7 this single lesion continued, with no lesions or symptoms of infection in the other four animals.

In group B, no lesions or symptoms of genital HSV-2 infection were observed throughout the seven day observation, with the exception of a lesion which appeared on one animal on the fifth day. This lesion was no longer observable by the sixth day.

In group C, a single lesion was noted on the fourth day, and two animals evidenced infection on the fifth day. On the sixth and seventh days only a single, borderline lesion was observable.

When a lesion was observed in a treated animal, there was no evidence of the spreading, genital swelling, exudation, etc. observed in control animals. No detrimental adverse reactions were observed in groups A, B and C, other than mild hyperkeratosis noted in some of the animals.

What is claimed is:

1. A method for inhibiting enveloped viruses on non-living substrates which comprises contacting an enveloped virus and a non-living substrate contaminated therewith, with an effective virus inhibiting amount of a phenylketone compound or pharmacologically-acceptable salt thereof, said phenylketone compound corresponding to one of the formulae:

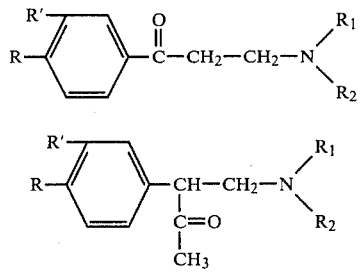

wherein R represents hydrogen, halo, or alkoxy of from one to twelve carbon atoms, R' represents hydrogen or halo; $R_1$ and $R_2$ represent loweralkyl, or $R_1$ and $R_2$ taken together with the nitrogen atom represent a heterocyclic amino group or an N-alkyl quaternary heterocyclic ammonium group having four, five or six carbon atoms and zero or one additional ring hetero atom selected from oxygen, sulfur and nitrogen or $R_1$ and $R_2$, taken together with the nitrogen atom represent triloweralkylammonium.

2. Method of claim 1 wherein the virus is a herpes virus.

3. Method of claim 1 wherein the virus is herpes simplex virus type 1.

4. Method of claim 1 wherein the virus is herpes simplex virus type 2.

5. Method of claim 1 wherein the virus is influenza virus.

6. Method of claim 1 wherein $R_1$ and $R_2$ taken together with the nitrogen atom represent piperidino.

7. Method of claim 1 wherein the phenylketone compound corresponds to formula I, R' is hydrogen, R is alkoxy and $R_1$ and $R_2$, taken together with the nitrogen atom represent piperidino.

8. Method of claim 7 wherein the compound is dyclonine hydrochloride.

9. A method for inhibiting enveloped viruses which comprises contacting enveloped viruses with an effective virus inhibiting amount of a phenylketone compound or pharmacologically-acceptable salt thereof, said phenylketone compound corresponding to one of the formulae:

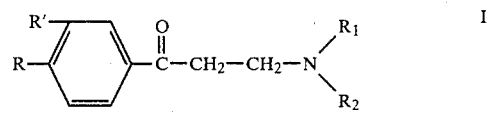

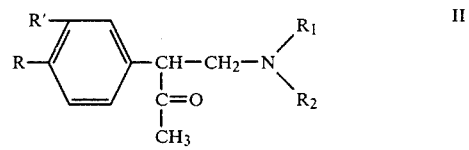

wherein R represents hydrogen, halo, or alkoxy of from one to twelve carbon atoms, R' represents hydrogen or halo; $R_1$ and $R_2$ represent loweralkyl, or $R_1$ and $R_2$ taken together with the nitrogen atom represent a heterocyclic amino group or N-alkyl quaternary heterocyclic ammonium group having four, five or six carbon atoms and zero or one additional ring hetero atom selected from oxygen, sulfur and nitrogen, or $R_1$ and $R_2$ taken together with the nitrogen represent triloweralkylammonium, with the proviso that, when the phenylketone compound corresponds to formula I, wherein R' is hydrogen and $R_1$ and $R_2$, taken together with the nitrogen atom represent piperidino, $R_2$ is other than n-butoxy.

10. Method of claim 9 wherein the phenylketone compound is a member of the group consisting of 4-methoxy-3-piperidino propiophenone, 3-phenyl-4-piperidino-2-butanone, 3',4'-dichloro-3-piperidinopropiophenone, 3'-chloro-3-piperidinopropiophenone, 4'-ethoxy-3-piperidinopropiophenone, 4'-propoxy-3-piperidinopropiophenone, 4'-isobutoxy-3-piperidinopropiophenone, 4'-hexyloxy-3-piperidinopropiophenone, 4'-n-octyloxy-3-piperidinopropiophenone, 4'-n-decyloxy-3-piperidinopropiophenone, 4'-butoxy-3-diethylaminopropiophenone, 4-butoxy-3-morpholinopropiophenone, and 1-[2-(4-butoxybenzoyl)-ethyl]-1-methyl piperidinium iodide.

11. Method of claim 9 wherein the virus is a herpes virus.

12. Method of claim 9 wherein R is n-decyloxy.

13. Method of claim 12 wherein the compound is 4'-n-decyloxy-3-piperidinopropiophenone hydrochloride.

14. A method for alleviating mammalian genital infections of herpes simplex virus type 2 which comprises contacting the genital mucoid cutaneous tissue of a mammal infected with said virus with an effective virus inhibiting amount of a compound selected from the group consisting of dyclonine and a pharmacologically acceptable salt thereof.

15. Method of claim 14 wherein the contacting is carried out by topically applying an effective virus inhibiting amount of said compound to herpes simplex virus type 2 infected genital mucoid cutaneous tissue, and repeating said topical application daily for at least three days.

16. Method of claim 15 wherein the compound is applied daily at a rate of from about three to about fifteen repeated applications per day.

17. Method of claim 14 wherein the contacting is carried out by topically applying the compound to intact mammalian genital tissue contaminated with said virus.

18. Method of claim 14 wherein the mammal is a male.

19. Method of claim 14 wherein the compound is applied to infected vulvular mucoid cutaneous tissue.

20. The method of claim 14 wherein the contacting is carried out by topically applying the compound to said tissues of said infected animal in the absence of lesions.

21. The method of claim 20 wherein the infection is asymptomatic.

22. Method of claim 14 wherein the compound is applied in the form of a composition containing about 2 percent of said compound in a pharmaceutical carrier.

23. A prophylactic method useful for inhibiting infection of mammals by enveloped viruses, which comprises topically applying an effective virus-inhibiting amount of a compound selected from the group consisting of dyclonine or a pharmaceutically-acceptable salt thereof to an uninfected mammal contaminated with said virus, in a manner effective to contact contaminating viruses on the cutaneous tissue of said mammal with said compound.

24. Method of claim 23 wherein the compound is topically applied in an amount insufficient to produce significant local anesthesia.

25. Method of claim 23 wherein the compound is applied to cutaneous tissue contaminated with herpes virus.

26. A method for inactivating herpes simplex virus type 2 which comprises contacting a herpes simplex virus type 2 with an effective virus inhibiting amount of composition containing about 2 percent of a compound selected from the group consisting of dyclonine and a pharmacologically-acceptable salt thereof, and a pharmaceutically-acceptable carrier.

* * * * *